US00PP20305P2

(12) United States Plant Patent
Talmadge

(10) Patent No.: US PP20,305 P2
(45) Date of Patent: Sep. 15, 2009

(54) ***SUTERA* PLANT NAMED 'BALABPINK'**

(50) Latin Name: *Sutera×hybrida*
Varietal Denomination: Balabpink

(75) Inventor: Paul A. Talmadge, Orcutt, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/218,441

(22) Filed: Jul. 15, 2008

(51) Int. Cl.
*A01H 5/00* (2006.01)

(52) U.S. Cl. ..... Plt./485

(58) Field of Classification Search ..... Plt./485
See application file for complete search history.

(56) References Cited

PUBLICATIONS

Canada Plant Breeders'Rights Application No. 08–6206 filed Feb. 28, 2008. Published information from web site attached http://www.inspection.gc.ca.

*Primary Examiner*—Kent L Bell
(74) *Attorney, Agent, or Firm*—Audrey Charles

(57) ABSTRACT

A new and distinct cultivar of *Sutera* plant named 'Balabpink', characterized by its lavender pink-colored flowers, medium green-colored foliage, and moderately vigorous, moderately compact, and trailing growth habit.

1 Drawing Sheet

Latin name of genus and species of plant claimed: *Sutera× hybrida.*
Variety denomination: 'Balabpink'.

BACKGROUND OF THE INVENTION

The present invention relates to a new and distinct cultivar of *Sutera* plant botanically known as *Sutera×hybrida* and hereinafter referred to by the cultivar name 'Balabpink'.

The new cultivar originated in a controlled breeding program in Guadalupe, Calif. during August 2005. The objective of the breeding program was the development of *Sutera* cultivars that continuously flower with attractive flower coloration, dark green-colored foliage, excellent basal branching, and spreading growth habit.

The new *Sutera* cultivar is the result of cross-pollination. The female (seed) parent of the new cultivar is the proprietary *Sutera×hybrida* breeding selection designated 5349-4-3, not patented, characterized by its dark lavender-colored flowers, medium green-colored foliage, and moderately vigorous, trailing growth habit. The male (pollen) parent of the new cultivar is 'Copia Pink', unpatented, characterized by its light pink-colored flowers, medium green-colored foliage, and moderately vigorous, trailing growth habit. The new cultivar was discovered and selected as a single flowering plant within the progeny of the above stated cross-pollination during April 2006 in a controlled environment at Guadalupe, Calif.

Asexual reproduction of the new cultivar by terminal stem cuttings since April 2006 at Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balabpink' as a new and distinct cultivar of *Sutera* plant:

1. Lavender pink-colored flowers;
2. Medium green-colored foliage; and
3. Moderately vigorous, moderately compact, and trailing growth habit.

Plants of the new cultivar differ from plants of the female parent primarily in flower color and growth habit and from plants of the male parent primarily in flower color and growth habit. The new cultivar has a more compact growth habit than either parent.

Of the many commercially available *Sutera* cultivars, the most similar in comparison to the new cultivar is Scopia Dark Pink 'Dancop19', U.S. Plant Pat. No. 18,116. However, in side by side comparisons, plants of the new cultivar differ from plants of 'Dancop19' in at least the following characteristics:

1. Plants of the new cultivar have a smaller flower diameter than plants of 'Dancop19'; and
2. Plants of the new cultivar have slightly lighter colored flowers than plants of 'Dancop19'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balabpink'. The plants were grown in 4.5 inch pots for 6 weeks in a greenhouse at West Chicago, Ill. Plants were given one pinch at transplant.

DETAILED BOTANICAL DESCRIPTION

Figure 1:
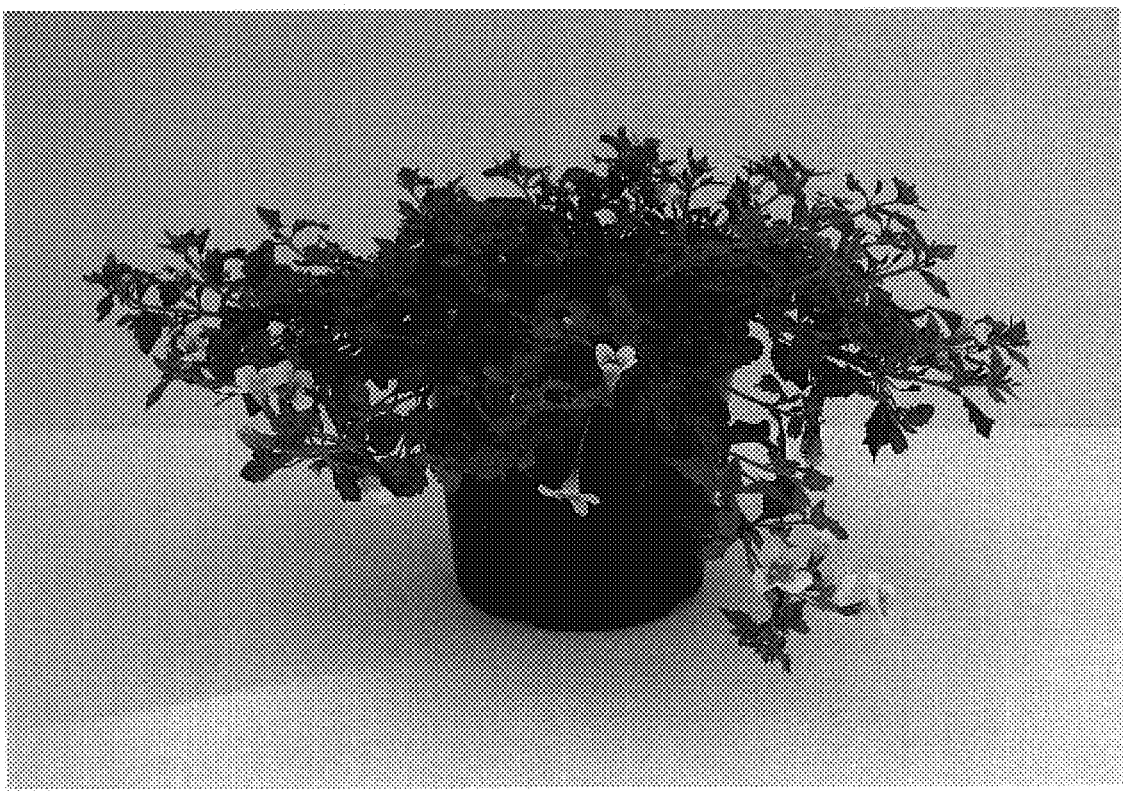
FIG. 1 illustrates a side view of the overall growth and flowering habit of 'Balabpink'.
Figure 2:
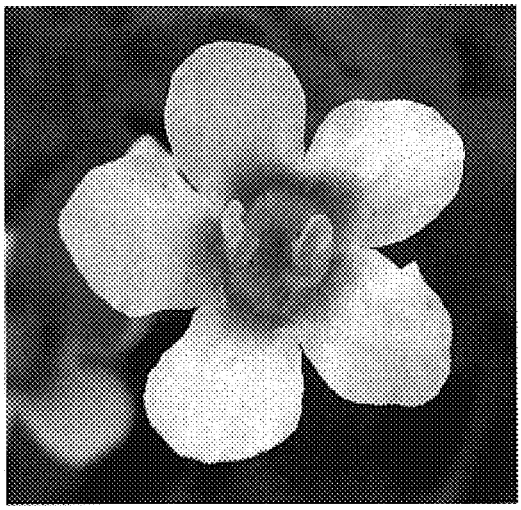
FIG. 2 illustrates a close-up view of an individual flower of 'Balabpink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Mar. 18, 2008 between 9:00 a.m. and 11:00 a.m. under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 6 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Sutera×hybrida* cultivar Balabpink.

Parentage:

*Female parent.*—Proprietary *Sutera×hybrida* breeding selection designated 5349-4-3, not patented.

*Male parent.*—'Copia Pink', unpatented.

Propagation:

*Type cutting.*—Terminal stem.

*Time to initiate roots.*—Approximately 10 to 13 days.

*Time to produce a rooted cutting.*—Approximately 21 to 24 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, moderately compact, trailing.

*Size.*—Height from soil level to top of plant plane: Approximately 6.3 cm. Width: Approximately 24.8 cm.

*Branching habit.*—Freely branching. Pinching will improve basal branching. Quantity of main branches per plant: Approximately 5.

*Branch.*—Strength: Strong, flexible. Length: Approximately 14.4 cm. Diameter: Approximately 1.5 mm. Length of central internode: Approximately 1.0 cm. Texture: Densely pubescent. Color of young and mature stems: 144A.

Foliage description:

*General description.*—Quantity of leaves per main branch: Approximately 16. Fragrance: None. Form: Simple. Arrangement: Opposite.

*Leaves.*—Aspect: Acute angle to stem; leaf blade transitions to an obtuse angle to stem with age. Shape: Broadly ovate. Margin: Serrate. Apex: Acute. Base: Attenuate. Venation pattern: Pinnate. Length of mature leaf: Approximately 1.8 cm. Width of mature leaf: Approximately 1.2 cm. Texture of upper and lower surfaces: Sparsely pubescent. Color of upper surface of young foliage: 137C with indistinguishable venation. Color of lower surface of young and mature foliage: 138B with venation of 138C. Color of upper surface of mature foliage 137A with indistinguishable venation.

*Petiole.*—Length: Approximately 3.5 mm. Diameter: Approximately 1.0 mm. Texture: Sparsely pubescent. Color: 138C.

Flowering description:

*Flowering habit.*—'Balabpink' is freely flowering under outdoor growing conditions with substantially continuous blooming from spring through autumn and year-round in greenhouse environment.

*Lastingness of individual flower on the plant.*—Approximately 6 to 9 days.

Flower description:

*General description.*—Type: Solitary, axillary, salverform and persistent. Quantity per plant: Approximately 14. Fragrance: None.

*Bud.*—Rate of opening: Generally takes 1 to 2 days for bud to progress from first color to fully open flower. Quantity per plant: Approximately 14.

*Bud just before opening.*—Shape: Obovoid. Length: Approximately 7.0 mm. Diameter: Approximately 3.0 mm. Texture: Densely glandular pubescent. Gland color: Colorless, transparent. Color: 76D.

*Corolla.*—Diameter: Approximately 1.5 cm.

*Petals.*—Quantity: 5, fused to form a tube. Shape: Obovate. Margin: Entire. Apex: Obtuse. Length from tube: Approximately 6.0 mm. Length of free portion: Approximately 5.0 mm. Width: Approximately 5.0 mm. Texture of upper and lower surfaces: Glabrous. Color of upper surface when first and fully open: 76B with 77B at tube opening. Color of lower surface when first and fully open: 76C.

*Corolla tube.*—Length: Approximately 7.0 mm. Diameter at distal end: Approximately 3.0 mm. Diameter at proximal end: Approximately 1.0 mm. Texture of inner surface: Densely pubescent. Texture of outer surface: Densely glandular pubescent. Gland color: Colorless, transparent. Color of inner surface: 77B at opening with throat of 16A. Color of outer surface: 158A with an overlay of 16B at distal end.

*Peduncle.*—Strength: Strong, flexible. Aspect: Acute angle to stem. Length: Approximately 1.2 cm. Diameter: Less than 1 mm. Texture: Densely pubescent. Color: 144A.

*Sepals.*—Quantity per flower: 5, fused at base. Shape: Narrow linear. Margin: Entire. Apex: Acute. Length: Approximately 4.0 mm. Width: Approximately 1.0 mm. Texture of upper surface: Sparsely pubescent. Texture of lower surface: Densely pubescent. Color of upper surface: 137A. Color of lower surface: 144A at base transitioning to 137A toward apex.

*Reproductive organs.*—Androecium: Stamen quantity: 4 didynamous, basifixed. Stamen length (longer pair): Approximately 9.0 mm. Filament length of free portion (longer pair): Approximately 4.0 mm. Stamen length (shorter pair): Approximately 6.0 mm. Filament length of free portion (shorter pair): Approximately 2.0 mm. Filament color: Purer white than 155D. Anther shape: Funnel. Anther length: Less than 1 mm. Anther color: 14C. Pollen amount: Abundant. Pollen color: 14A. Gynoecium: Pistil quantity: 1 per flower. Pistil length: Approximately 9.0 mm. Stigma shape: Elongated, curved. Stigma length: Approximately 1.0 mm. Stigma color: 144B. Style length: Approximately 7.0 mm. Style color: 144D. Ovary length: Approximately 1.0 mm. Ovary color: 144A.

Seed and fruit production: Neither seed nor fruit production has been observed.

Disease and pest resistance: Resistance to pathogens and pests common to *Sutera* has not been observed.

What is claimed is:

1. A new and distinct cultivar of *Sutera* plant named 'Balabpink', substantially as herein shown and described.

* * * * *